(12) United States Patent
Lai et al.

(10) Patent No.: US 12,076,364 B2
(45) Date of Patent: Sep. 3, 2024

(54) USE OF INTERFERENCE PEPTIDE IN PREPARATION OF ANTI-SARS-CoV-2 MEDICAMENT

(71) Applicant: KUNMING INSTITUTE OF ZOOLOGY, CHINESE ACADEMY OF SCIENCES, Yunnan (CN)

(72) Inventors: Ren Lai, Yunnan (CN); Xiaopeng Tang, Yunnan (CN); Zhiyi Liao, Yunnan (CN)

(73) Assignee: KUNMING INSTITUTE OF ZOOLOGY, CHINESE ACADEMY OF SCIENCES, Yunnan (CN)

(*) Notice: Subject to any disclaimer, the term of this patent is extended or adjusted under 35 U.S.C. 154(b) by 308 days.

(21) Appl. No.: 17/428,024

(22) PCT Filed: Jun. 22, 2020

(86) PCT No.: PCT/CN2020/097446
§ 371 (c)(1),
(2) Date: Aug. 3, 2021

(87) PCT Pub. No.: WO2021/258250
PCT Pub. Date: Dec. 30, 2021

(65) Prior Publication Data
US 2022/0323537 A1 Oct. 13, 2022

(51) Int. Cl.
| *A61K 38/08* | (2019.01) |
| *A61K 38/07* | (2006.01) |
| *A61K 38/10* | (2006.01) |
| *A61P 31/14* | (2006.01) |
| *C07K 7/06* | (2006.01) |
| *C07K 7/08* | (2006.01) |

(52) U.S. Cl.
CPC ............. *A61K 38/08* (2013.01); *A61K 38/07* (2013.01); *A61K 38/10* (2013.01); *A61P 31/14* (2018.01)

(58) Field of Classification Search
CPC ........ A61K 38/08; A61K 38/07; A61K 38/10; A61P 31/14; C07K 7/06; C07K 7/08
See application file for complete search history.

(56) References Cited

U.S. PATENT DOCUMENTS

| 7,592,143 B2* | 9/2009 | Kasibhatla | ......... A61K 49/0052 |
| | | | 435/7.1 |
| 10,143,187 B2* | 12/2018 | Dennis | ............... G01N 33/5308 |
| 10,706,955 B2* | 7/2020 | Bremel | .................. G16B 20/00 |
| 10,722,576 B2* | 7/2020 | Häsler | ...................... C07K 16/40 |
| 2002/0102610 A1 | 8/2002 | Townsend et al. | |
| 2003/0211116 A1* | 11/2003 | White | ............... C07K 14/70539 |
| | | | 435/325 |

FOREIGN PATENT DOCUMENTS

| CN | 1488641 A | 4/2004 |
| CN | 104072592 A | 10/2014 |
| CN | 107022008 A | 8/2017 |
| CN | 107245095 A | 10/2017 |
| CN | 107952080 A | 4/2018 |
| CN | 110128510 A | 8/2019 |
| WO | 2005080419 A1 | 9/2005 |
| WO | 2016077840 A2 | 5/2016 |
| WO | 2020124032 A1 | 6/2020 |

OTHER PUBLICATIONS

Tan et al., "Transferrin receptor is another receptor for SARS-CoV-2 entry," bioRxiv, Oct. 23, 20202, pp. 1-26. (Year: 2020).*
International Search Report dated Mar. 25, 2021 for International Application No. PCT/CN2020/097446, 8 pages.
Office Action (with English translation) issued in Chinese Patent Application No. 202010574448.X on Dec. 31, 2020, 13 pages.
First Search (with English translation) issued in Chinese Patent Application No. 202010574448.X on Dec. 23, 2020, 6 pages.
Cavezzi et al., COVID-19: hemoglobin, iron, and hypoxia beyond inflammation. A narrative review. Clinics and Practice 2020; 10:1271 (May 28, 2020), pp. 24-30.
Venter et al., GenBank Accession No. EAW53671, transferrin receptor (p90, CD71), isoform CRA_b [*Homo sapiens*] https://www.ncbi.nlm.nih.gov/protein/EAW53671.1?report=genbank&log$=protalign&blast_rank=1&RID=Y581ND0Z01R (Mar. 23, 2015) pp. 1-2.

* cited by examiner

*Primary Examiner* — Julie Ha
(74) *Attorney, Agent, or Firm* — MH2 TECHNOLOGY LAW GROUP, LLP

(57) ABSTRACT

An agent for inhibiting binding of transferrin receptor to SARS-CoV-2 spike protein or an anti-SARS-CoV-2 medicament is provided, where active pharmaceutical ingredients of the agent or the medicament include interference peptides, and the interference peptides include: SL8, FG8, DL12, RK4, SD6, HF7, and/or QK8.

2 Claims, 9 Drawing Sheets

Specification includes a Sequence Listing.

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Amino acid sequence of SL8

<400> SEQUENCE: 1

Ser Lys Val Glu Lys Leu Thr Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Amino acid sequence of FG8

<400> SEQUENCE: 2

Phe Pro Phe Leu Ala Tyr Ser Gly
1               5

<210> SEQ ID NO 3
<211> LENGTH: 12
<212> TYPE: PRT
<213> ORGANISM: Artificial Sequence
<220> FEATURE:
<223> OTHER INFORMATION: Amino acid sequence of DL12

<400> SEQUENCE: 3

Asp Gln Thr Lys Phe Pro Ile Val Asn Ala Glu Leu
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Amino acid sequence of RK4

<400> SEQUENCE: 4

Arg Ala Gly Lys
1

<210> SEQ ID NO 5
<211> LENGTH: 6
<212> TYPE: PRT
<213> ORGANISM: Artificial Sequence
<220> FEATURE:
<223> OTHER INFORMATION: Amino acid sequence of SD6

<400> SEQUENCE: 5
```

-continued

```
Ser Asp Trp Lys Thr Asp
1               5

<210> SEQ ID NO 6
<211> LENGTH: 7
<212> TYPE: PRT
<213> ORGANISM: Artificial Sequence
<220> FEATURE:
<223> OTHER INFORMATION: Amino acid sequence of HF7

<400> SEQUENCE: 6

His Pro Val Thr Gly Gln Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Amino acid sequence of QK8

<400> SEQUENCE: 7

Gln Asp Ser Asn Trp Ala Ser Lys
1               5

<210> SEQ ID NO 8
<211> LENGTH: 22
<212> TYPE: DNA
<213> ORGANISM: Artificial Sequence
<220> FEATURE:
<223> OTHER INFORMATION: Forward primer for qRT-PCR

<400> SEQUENCE: 8
ggggaacttc tcctgctaga at                                              22

<210> SEQ ID NO 9
<211> LENGTH: 22
<212> TYPE: DNA
<213> ORGANISM: Artificial Sequence
<220> FEATURE:
<223> OTHER INFORMATION: Reverse primer for qRT-PCR

<400> SEQUENCE: 9
cagacatttt gctctcaagc tg                                              22

<210> SEQ ID NO 10
<211> LENGTH: 20
<212> TYPE: DNA
<213> ORGANISM: Artificial Sequence
<220> FEATURE:
<223> OTHER INFORMATION: Probe primer for qRT-PCR

<400> SEQUENCE: 10
ttgctgctgc ttgacagatt                                                 20
```

USE OF INTERFERENCE PEPTIDE IN PREPARATION OF ANTI-SARS-CoV-2 MEDICAMENT

CROSS-REFERENCE TO RELATED APPLICATIONS

This application is the National Phase of PCT International Application No. PCT/CN2020/097446, filed on Jun. 22, 2020, the contents of which are hereby expressly incorporated by reference in its entirety.

SEQUENCE LISTING

The instant application contains a Sequence Listing which has been submitted electronically in ASCII format and is hereby incorporated by reference in its entirety. Said ASCII copy, created on 6 Jul. 2021, is named SequenceListing.txt and is 3 kilobytes in size.

TECHNICAL FIELD

The present disclosure belongs to the technical field of medicine, and specifically relates to use of interference peptides in the preparation of an anti-SARS-CoV-2 medicament.

BACKGROUND ART

The SARS-CoV-2 pandemic has caused a serious public health emergency. The SARS-CoV-2 is an enveloped virus with a positive RNA genome and belongs to the subfamily Coronavirinae in the family Coronaviridae of the order Nidovirales. CoV particle at least includes four structural proteins: spike (S), envelope (E), membrane (M), and nucleocapsid (N). Transmembrane spike protein (S-protein) is a viral fusion protein, by which a coronavirus enters a host cell in an S-protein-medicated manner to form a homotrimer on the viral surface. The S-protein includes two functional subunits that are responsible for binding to a host cell receptor S1 subunit and S2 subunits of a fused virus and a cell membrane. Therefore, the S-protein determines host range and cell orientation. Further, the S-protein is not only a major target of an activated neutralizing antibody during infection, but also a focus on vaccine design. However, there is no approval of any therapy or vaccine against SARS-CoV-2 infected in human at present.

SUMMARY

In view of this, an objective of the present disclosure is to provide use of interference peptides in the preparation of an anti-SARS-CoV-2 medicament that has an antiviral effect; the interference peptides are conveniently prepared, low-cost, and suitable for medicaments.

To achieve the above objective, the present disclosure provides the following technical solutions:

The present disclosure provides use of interference peptides in the preparation of an anti-SARS-CoV-2 medicament, and the interference peptides include: SL8, FG8, DL12, RK4, SD6, HF7, and/or QK8;

the SL8 has an amino acid sequence as shown in SEQ ID NO. 1, the FG8 has an amino acid sequence as shown in SEQ ID NO. 2, the DL12 has an amino acid sequence as shown in SEQ ID NO. 3, the RK4 has an amino acid sequence as shown in SEQ ID NO. 4, the SD6 has an amino acid sequence as shown in SEQ ID NO. 5, the HF7 has an amino acid sequence as shown in SEQ ID NO. 6, and the QK8 has an amino acid sequence as shown in SEQ ID NO. 7.

The present disclosure further provides an agent for inhibiting binding of transferrin receptor to SARS-CoV-2 spike protein, where active pharmaceutical ingredients of the agent include interference peptides, and the interference peptides include: SL8, FG8, DL12, RK4, SD6, HF7, and/or QK8;

the SL8 has an amino acid sequence as shown in SEQ ID NO. 1, the FG8 has an amino acid sequence as shown in SEQ ID NO. 2, the DL12 has an amino acid sequence as shown in SEQ ID NO. 3, the RK4 has an amino acid sequence as shown in SEQ ID NO. 4, the SD6 has an amino acid sequence as shown in SEQ ID NO. 5, the HF7 has an amino acid sequence as shown in SEQ ID NO. 6, and the QK8 has an amino acid sequence as shown in SEQ ID NO. 7.

Preferably, the interference peptides may have a working concentration of 0.5-5 µM/60 nM SARS-CoV-2 spike protein.

The present disclosure further provides an anti-SARS-CoV-2 medicament, where active pharmaceutical ingredients of the medicament include interference peptides, and the interference peptides include: SL8, FG8, DL12, RK4, SD6, HF7, and/or QK8;

the SL8 has an amino acid sequence as shown in SEQ ID NO. 1, the FG8 has an amino acid sequence as shown in SEQ ID NO. 2, the DL12 has an amino acid sequence as shown in SEQ ID NO. 3, the RK4 has an amino acid sequence as shown in SEQ ID NO. 4, the SD6 has an amino acid sequence as shown in SEQ ID NO. 5, the HF7 has an amino acid sequence as shown in SEQ ID NO. 6, and the QK8 has an amino acid sequence as shown in SEQ ID NO. 7.

Compared with the prior art, the present disclosure has the following beneficial effects:

The present disclosure provides use of interference peptides in the preparation of an anti-SARS-CoV-2 medicament, and the interference peptides are designed based on a binding site of transferrin receptor to SARS-CoV-2 spike protein and can effectively treat SARS-CoV-2-infected cells. In the examples of the present disclosure, SPR has verified that all of seven interference peptides designed can significantly inhibit the binding of SARS-CoV-2 spike protein to transferrin receptor and thus inhibit SARS-CoV-2 infection.

DETAILED DESCRIPTION OF THE EMBODIMENTS

Figure 1:
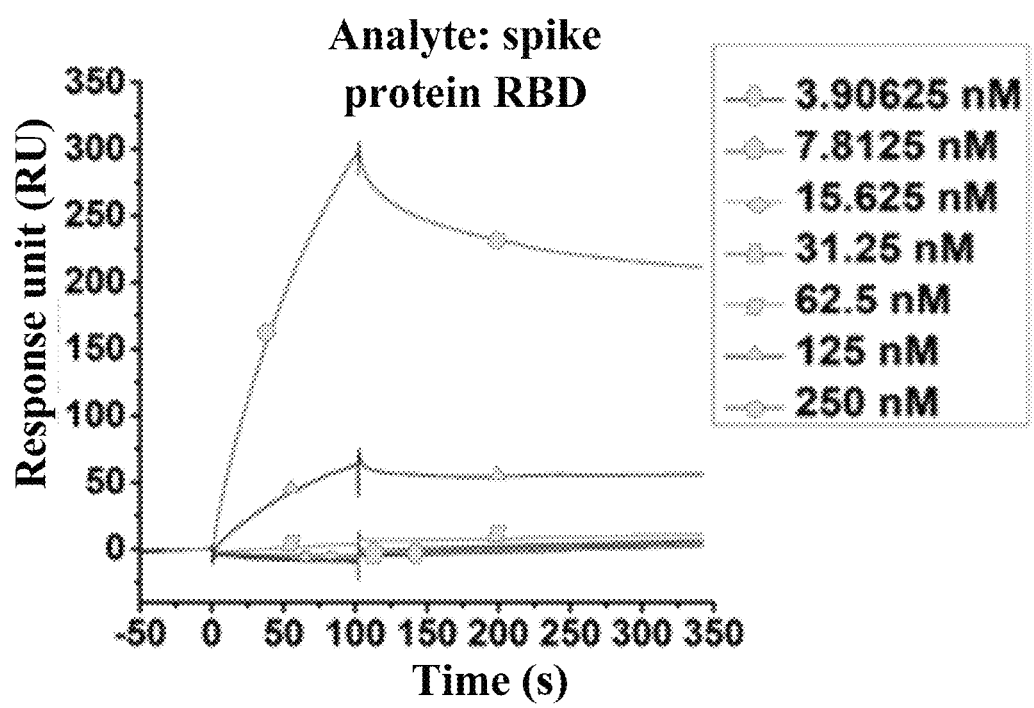
FIG. 1 illustrates a verification of the binding of SARS-CoV-2 spike protein receptor-binding domain (RBD) to transferrin receptor by using surface plasmon resonance (SPR); curves, from top to bottom, represent spike protein concentrations of 250 nM, 125 nM, 62.5 nM, 31.25 nM, 15.625 nM, 7.8125 nM, and 3.90625 nM, respectively.

The present disclosure will be further described below with reference to examples.

The present disclosure provides use of interference peptides in the preparation of an anti-SARS-CoV-2 medicament, and the interference peptides include: SL8, FG8, DL12, RK4, SD6, HF7, and/or QK8;

the SL8 has an amino acid sequence as shown in SEQ ID NO. 1, the FG8 has an amino acid sequence as shown in SEQ ID NO. 2, the DL12 has an amino acid sequence as shown in SEQ ID NO. 3, the RK4 has an amino acid sequence as shown in SEQ ID NO. 4, the SD6 has an amino acid sequence as shown in SEQ ID NO. 5, the HF7 has an amino acid sequence as shown in SEQ ID NO. 6, and the QK8 has an amino acid sequence as shown in SEQ ID NO. 7.

The information on sequences of the interference peptides of the present disclosure is shown in Table 1:

TABLE 1

The sequences of the interference peptides

| Peptide name | Sequence | SEQ ID NO. |
|---|---|---|
| SL8 | SKVEKLTL | 1 |
| FG8 | FPFLAYSG | 2 |
| DL12 | DQTKFPIVNAEL | 3 |
| RK4 | RAGK | 4 |
| SD6 | SDWKTD | 5 |
| HF7 | HPVTGQF | 6 |
| QK8 | QDSNWASK | 7 |

Preparation methods of the interference peptides are not particularly limited in the present disclosure, and the interference peptides may preferably be prepared by artificial synthesis. In the present disclosure, the transferrin receptor may bind to the SARS-CoV-2 spike protein and thus infect human cells; the interference peptides may inhibit the binding of the transferrin receptor to the SARS-CoV-2 spike protein, thereby achieving anti-SARS-CoV-2 and SARS-CoV-2 infection-treating effects.

The present disclosure further provides an agent for inhibiting binding of transferrin receptor to SARS-CoV-2 spike protein, where active pharmaceutical ingredients of the agent include interference peptides, and the interference peptides include: SL8, FG8, DL12, RK4, SD6, HF7, and/or QK8;

the SL8 has an amino acid sequence as shown in SEQ ID NO. 1, the FG8 has an amino acid sequence as shown in SEQ ID NO. 2, the DL12 has an amino acid sequence as shown in SEQ ID NO. 3, the RK4 has an amino acid sequence as shown in SEQ ID NO. 4, the SD6 has an amino acid sequence as shown in SEQ ID NO. 5, the HF7 has an amino acid sequence as shown in SEQ ID NO. 6, and the QK8 has an amino acid sequence as shown in SEQ ID NO. 7.

In the present disclosure, the interference peptides may preferably have a working concentration of 0.5-5 µM/60 nM SARS-CoV-2 spike protein. In the present disclosure, the active pharmaceutical ingredients of the agent may be either a single interference peptide or a mixture of more interference peptides, and further, the mixing ratio of all interference peptides in the mixture is not particularly limited, as long as total concentration may reach 0.5-5 µM/60 nM SARS-CoV-2 spike protein.

The present disclosure further provides an anti-SARS-CoV-2 medicament, where active pharmaceutical ingredients of the medicament include interference peptides, and the interference peptides include: SL8, FG8, DL12, RK4, SD6, HF7, and/or QK8;

the SL8 has an amino acid sequence as shown in SEQ ID NO. 1, the FG8 has an amino acid sequence as shown in SEQ ID NO. 2, the DL12 has an amino acid sequence as shown in SEQ ID NO. 3, the RK4 has an amino acid sequence as shown in SEQ ID NO. 4, the SD6 has an amino acid sequence as shown in SEQ ID NO. 5, the HF7 has an amino acid sequence as shown in SEQ ID NO. 6, and the QK8 has an amino acid sequence as shown in SEQ ID NO. 7. The working concentrations and the mixing ratio of the interference peptides of the present disclosure are the same as those described above, and the details will not be repeated herein.

Pharmaceutical dosage forms of the medicament of the present disclosure are not particularly limited, preferably including powder, tablet, granules, capsule, solution, emulsion, suspension, or injection. The medicament of the present disclosure further includes pharmaceutically acceptable excipients. In the present disclosure, when the pharmaceutical dosage forms of the medicament are prepared, the medicament may preferably be prepared according to the preparation methods of different pharmaceutical dosage forms.

The present disclosure further provides a method for treating SARS-CoV-2-infected cells, i.e., the SARS-CoV-2-infected cells are mixed with the interference peptides, where the mixing ratio of the cells to the peptides may be $4 \times 10^4$ cells: 800 nM.

The present disclosure further provides a method for treating diseases caused by SARS-CoV-2 infection, i.e., the foregoing interference peptides are injected intravenously, where the interference peptides may preferably have an injection dose of 0.5-1 mg/kg. In the present disclosure, during the intravenous injection, a single polypeptide may preferably be injected.

The use of interference peptides in the preparation of an anti-SARS-CoV-2 medicament provided by the present invention will be described in detail below with reference to the examples, but they should not be construed as limiting the protection scope of the present disclosure.

Example 1

Verification of the Binding of SARS-CoV-2 Spike Protein RBD to Transferrin Receptor by SPR Transferrin receptor (11020-H07H, Sino biological, China) was diluted (20 µg/ml) with 200 µl of sodium acetate buffer (10 mM, pH 5), and flew through a CMS sensor chip (BR100012, GE, USA) at a flow rate of 5 µl/min to reach 2,000 resonance units (RU). The remaining active sites on the chip were blocked with 75 µl of ethanolamine solution (1 M, pH 8.5). The interactions between serial concentrations of spike protein RBD (3.90625, 7.8125, 15.625, 31.25, 62.5, 125, and 250 nM) in Tris-HCl buffer (20 mM, pH 7.4) and immobilized transferrin receptor were analyzed at a flow rate of 10 µl/min. The BIA software (GE, USA) was used to determine the bound KD and the rate constants Ka and Kd. Results are shown in FIG. 1. The binding ability of the SARS-CoV-2 spike protein RBD to the transferrin receptor is strong, and Ka, Kd, and KD are $9.36\times10^4$ $M^{-1}s^{-1}$, $4\times10^{-3}s^{-1}$, and 43 nM, respectively.

Example 2

Figure 2:
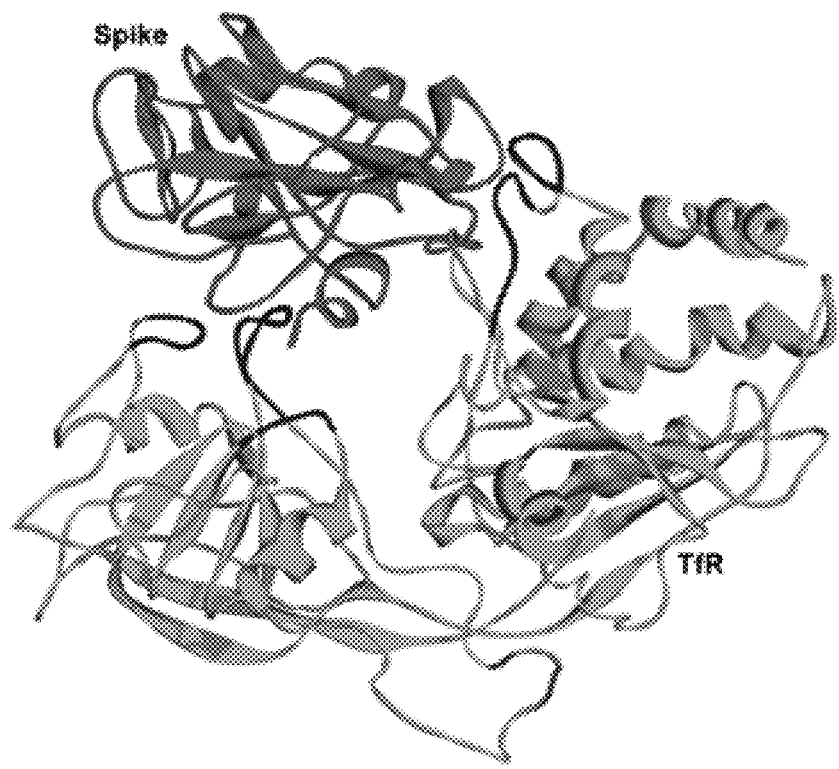
FIG. 2 illustrates a protein-protein docking analysis of a binding site of SARS-CoV-2 spike protein to transferrin receptor.

Prediction of SARS-CoV-2 Spike Protein-Transferrin Receptor by Protein-Protein Docking Analysis Well-known transferrin receptor crystal structure (PDB ID: 1CX8) and SARS-CoV-2 spike protein crystal structure (PDB ID: 6LZG) were used, and protein-protein docking analysis was conducted by using ZDOCK. Results are shown in FIG. 2. Molecular docking results show an interaction between transferrin receptor and spike protein RBD.

Example 3

Chemical Preparation Method of Interference Peptides, Synthesized by Fmoc-Lys(Boc)-Wang Resin 1. Resin Swelling 5 g of Fmoc-Leu-Wang Resin with a degree of substitution of 0.3 was weighed, poured into a reaction column, swollen with 50 ml of DCM, and soaked for 30 min.

2. Deprotection

The DCM in the reaction column was suctioned to dryness; Fmoc was removed with 20% piperidine in DMF; nitrogen was blown for 30 min; after suctioning to dryness, the reaction column was washed with DMF five times, and the DMF was suctioned to dryness.

3. Condensation Reaction

Condensation was conducted with a combination of TBTU/DIEA activators; TBTU and linking amino acids were calculated and weighed based on 3-fold feed capacity, dissolved in 50 ml of DMF, and charged into the reaction column; DIEA (1.55 ml) was added, nitrogen was blown, and the reaction was conducted for 1 h.

4. Detection and Washing

A little resin was sampled from the reaction column using a sampling tube, decanted into a small test tube, and washed once with DMF; after DMF was discarded, three drops each of solutions A, B, and C (solution A: ninhydrin in ethanol, solution B: mixture of 20% ethanol and 80% phenol, solution C: redistilled pyridine) were charged into the small test tube, and the small test tube was placed and heated in a heater at 120° C. for 3 min; after removing the small test tube, colors of the solution and the resin were observed, where a yellow solution and colorless or yellowish resin indicate a complete condensation reaction; the reaction in the reaction column was stopped, the solution was suctioned to dryness, and the reaction column was washed with DMF thrice.

5. Refeeding

If the resin color is detected as other colors, e.g., green, blue, and purple, the reaction may be incomplete. Similarly, suctioning and washing were conducted thrice; the same amounts of reactants as the current reaction were weighed and poured into the reaction column to react again, until a complete reaction was detected.

6. Continuous Condensation

For subsequent linkage of amino acids, steps 2 to 5 were repeated; the amounts of different amino acids to be weighed were calculated and weighed according to the same calculation method; the amount of TBTU/DIEA remained unchanged.

7. Shrinkage

After the completion of the linkage of the last amino acid, step 2 was repeated; the reaction column was washed with DCM thrice and methanol thrice, and suctioned to dryness; the resin was poured out, dried over a drying lamp, and filled in a 500 ml beaker.

8. Cleavage 100 ml of cleavage cocktail (TFA/thioanisole/phenol/EDT/water=86/5/4/3/2) was charged into a beaker; the beaker was placed on a magnetic stirrer, a magneton was put in the beaker, and the reaction was conducted for 2 h under stirring; after that, the resin was filtered through a sand core funnel and rinsed with TFA twice; the cleavage cocktail was decanted into 600 ml of ice ether, during which polypeptides were precipitated to form a polypeptide ether suspension; a large centrifuge was used for repeated centrifugation, respectively; the supernatant was discarded, and precipitates were washed with ether thrice and baked over a drying lamp to remove residual ether; the resulting solid was a target crude polypeptide product.

9. Purification

The crude product was dissolved in water, filtered, and separated and purified by high performance liquid chromatography (HPLC), and finally a target fine polypeptide product with a purity of over 95% was obtained.

10. Preparation 7 g of crude product was dissolved in a solution of ACN:$H_2O$ 1:4 (V/V), and a small portion of the sample was collected to analyze the peak time of the sample. (HPLC was conducted by a high performance liquid chromatograph) Cartridges for preparing the 100DAC column were selected; the sample was injected into the column, and a gradient was selected for separation according to the peak time of the crude product; impurities were separately collected according to the HPLC chart; LC-MS was used to determine whether the products collected were necessary or not, and the necessary substances were left for detection. Products qualified in HPLC were subjected to rotary evaporation and lyophilization. An amount of desired product (white powder) was obtained.

Example 4

Verification of the Inhibition of Interference Peptides against the Binding of SARS-CoV-2 Spike Protein to Transferrin Receptor by SPR Spike proteins (60 nM) doped with different concentrations (0.5 and 5 μM) of interference peptides were injected at a flow rate of 20 μl/min to detect the inhibition of interference peptides against the binding of spike protein to transferrin receptor.

Figure 3:
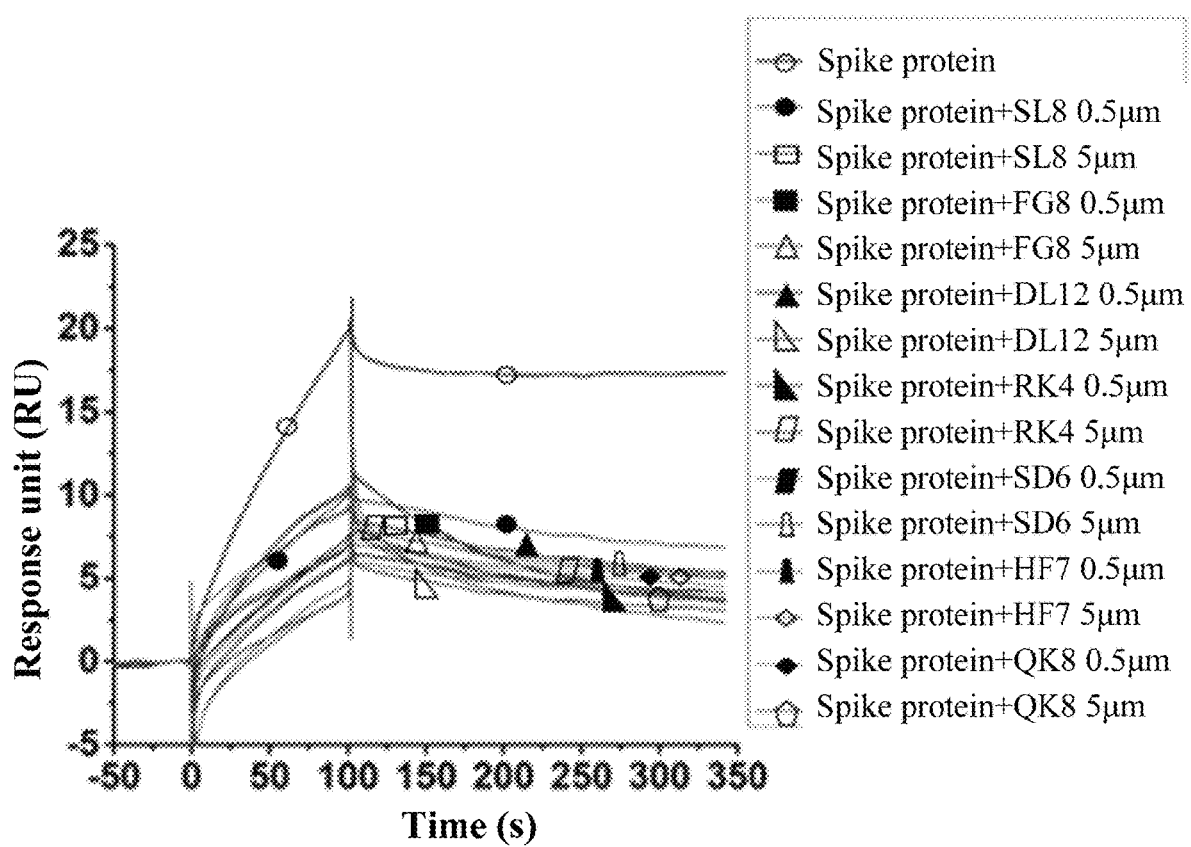
FIG. 3 illustrates a verification of an ability of interference peptides to inhibit the binding of SARS-CoV-2 spike protein to transferrin receptor by SPR.
Figure 4:
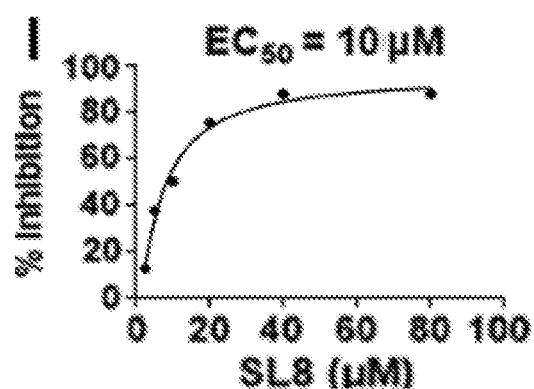
FIG. 4(a)-(g) illustrates a comparison of inhibition of SARS-COV-2-infected Vero-E6 cells by interference peptides SL8, FG8, DL12, RK4, SD6, HF7 and QK8 in different concentrations, respectively.
Figure 4:
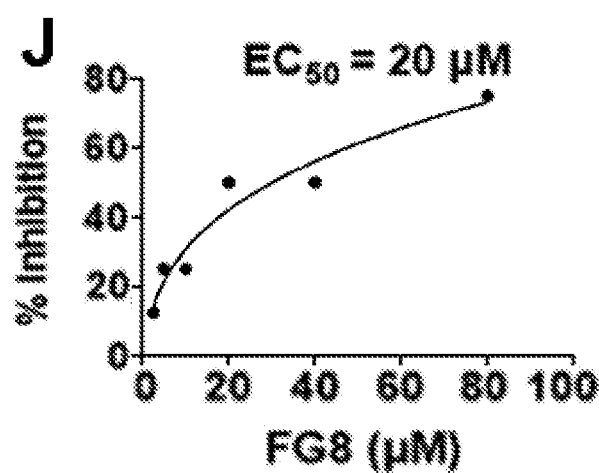
Figure 4:
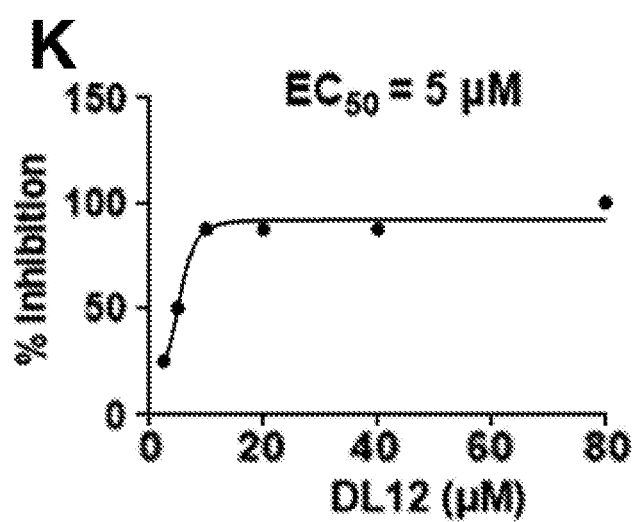
Figure 4:
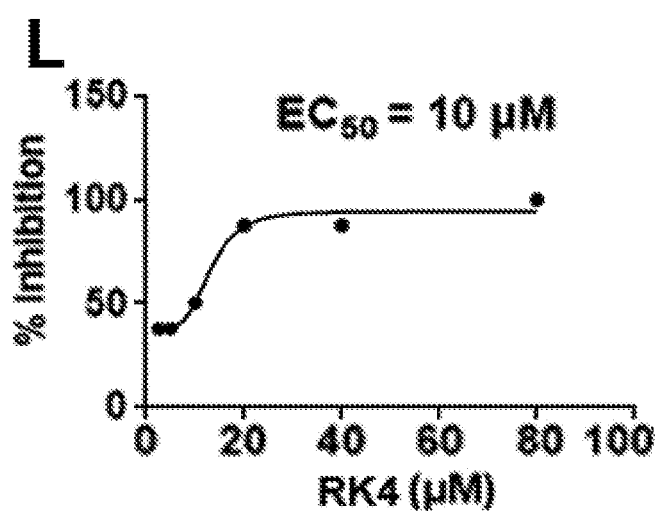
Figure 4:
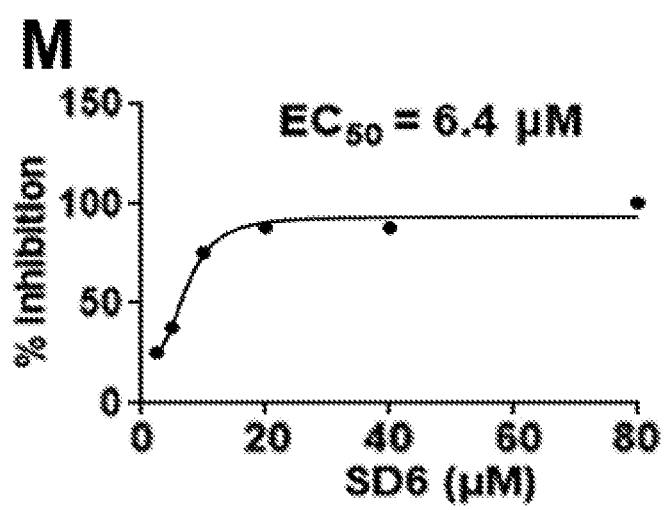
Figure 4:
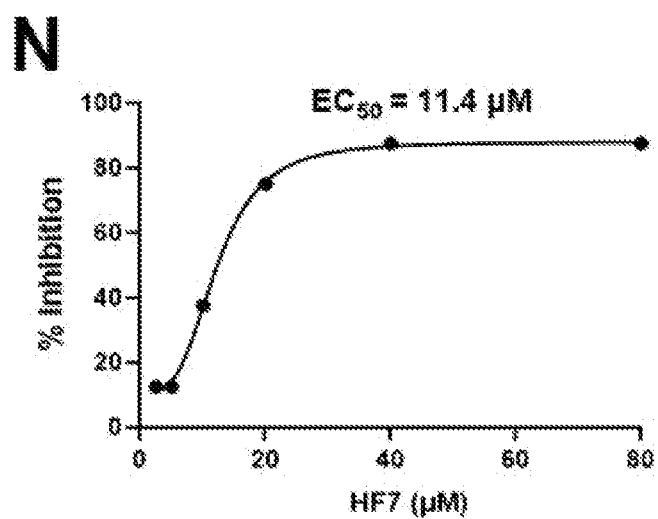
Figure 4:
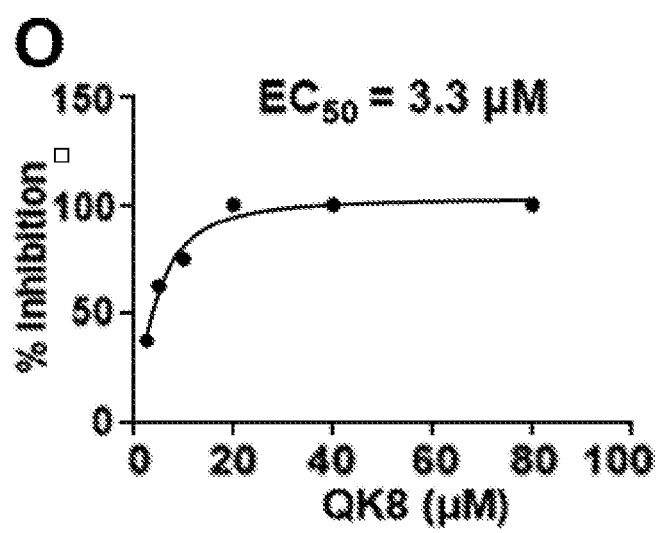

Results are shown in FIG. 3. Seven interference peptides significantly inhibit the binding of SARS-CoV-2 spike protein to transferrin receptor.

Example 5

Inhibition of Interference Peptides Against SARS-CoV-2-Infected Vero E6 Cells

Vero E6 cells (from Kunming Cell Bank) were pre-treated with different interference peptides for 1 h and infected with SARS-CoV-2 for 1 h. Subsequently, a virus-interference peptides mixture was removed, and the cells were further cultured with a fresh medium supplemented with interference peptides. At 48 h, a cell supernatant was collected, and lysed with Cell Lysis Buffer (Cat #15596018, Thermo, USA) to conduct further cytopathogenic effect (CPE) and quantitative RT-PCR (qRT-PCR) analysis.

Amplified primers used in qRT-PCR were NP gene primers:

Target-2-F (SEQ ID NO. 8): GGG-GAACTTCTCCTGCTAGAAT,

Target-2-R (SEQ ID NO. 9): CAGACATTTTGCTCT-CAAGCTG, and

Target-2-P (SEQ ID NO. 10): 5'-FAM-TTGCTGCTGCTTGACAGATT-TAMRA-3'.

Results are shown in FIG. 4(a)-(g). Seven interference peptides can inhibit SARS-CoV-2 infection; at a concentration of 80 μM, SL8, FG8, DL12, RK4, SD6, HF7, and QK8 inhibit 87%, 75%, 99%, 99%, 98%, 89%, and 99% of viral infection, respectively, and median inhibitory concentrations (EC50) of the seven polypeptides are 10, 20, 5, 10, 6.4, 11.4, and 3.3 μM, respectively.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for treating a SARS-COV-2 infection in a patient, the method comprising: injecting an agent intravenously to the patient in need thereof, wherein the agent comprises an interference peptide as an active ingredient, and the interference peptide comprises QK8; and the QK8 has an amino acid sequence as shown in SEQ ID NO: 7.

2. The method according to claim 1, wherein the method comprises injecting the interference peptide in a dose range of 0.5-1 mg/kg of body weight.

* * * * *